United States Patent [19]

Arnold et al.

[11] 4,365,154
[45] Dec. 21, 1982

[54] DETECTION OF IMPURITIES IN A FLUID CONTAINING FREE GAS USING NUCLEAR TECHNIQUES

[75] Inventors: Dan M. Arnold; Hans J. Paap, both of Houston, Tex.

[73] Assignee: Texaco Inc., White Plains, N.Y.

[21] Appl. No.: 127,700

[22] Filed: Mar. 6, 1980

[51] Int. Cl.³ .................. G01V 5/00; G01T 1/169
[52] U.S. Cl. ........................ 250/270; 250/301; 250/432 R
[58] Field of Search ............ 250/359, 270, 435, 301, 250/432 R, 436, 360, 269, 253, 255, 261

[56] References Cited

U.S. PATENT DOCUMENTS

| | | | |
|---|---|---|---|
| 2,873,377 | 2/1959 | McKay | 313/93 |
| 4,191,884 | 3/1980 | Scott | 250/270 |
| 4,209,695 | 6/1980 | Arnold et al. | 250/270 |

FOREIGN PATENT DOCUMENTS

7759  2/1980  European Pat. Off. ............ 250/301

*Primary Examiner*—Alfred E. Smith
*Assistant Examiner*—Carolyn E. Fields
*Attorney, Agent, or Firm*—Robert A. Kulason; Jack H. Park

[57] ABSTRACT

Fluid containing free gas and in a pipeline or container at a refinery or at any of various petroleum producing operations is bombarded with neutrons and high energy gamma rays resulting from capture of thermal neutrons are detected. The spectra of the detected gamma rays are then analyzed to determine the concentration of the elements chlorine and hydrogen. The counting rate for thermal neutron gamma rays for hydrogen permits a measure of the hydrogen index (HI) of the fluid to be obtained. The hydrogen index and the relative concentrations of chlorine and hydrogen are used to obtain an indication of the presence and concentration of chlorine or salt water in the fluid.

18 Claims, 11 Drawing Figures

$R_S$ vs $R_{Cl}$ vs $C_H$
FOR VARIOUS VALUES OF $M_S$, $M_{Cl}$, AND HI

DETECTION OF IMPURITIES IN A FLUID CONTAINING FREE GAS USING NUCLEAR TECHNIQUES

BACKGROUND OF THE INVENTION

1. Field of Invention

The present invention relates to nuclear techniques for detecting impurities such as salt water and sulfur in petroleum refining and producing operations.

2. Description of Prior Art

U.S. Pat. No. 4,209,695 dated June 24, 1980, of common ownership to the present application, relates to a nuclear technique for measuring the chlorine and sulfur content of a flowing stream of fluid. However, the technique of this patent required that any free gas in the fluid be homogeneously mixed. Otherwise, any free gas in the stream of fluid introduced errors in the chlorine (and thus salt content) and sulfur measurements by varying the relative shielding properties of the fluid. Thus, for accurate results apparatus of the type in that patent was typically at the output of a gas-oil separator. There are, however, other locations in petroleum producing or refining operations where gas is present in the fluid and it is desirable to monitor the salt content of the fluid.

U.S. Pat. No. 4,200,789, dated Apr. 29, 1980 also of common ownership to the present application, relates to a technique for measuring oil and water cuts of a multiphase flowstream. The flowstream was bombarded with neutrons and high energy gamma rays resulting from the capture of thermal neutrons was detected. The spectra of the detected gamma rays were analyzed and the gamma ray counts of the element sulfur and the element chlorine determined. Since the gamma ray spectra of the element hydrogen was not needed or used, the effects of gas in the stream on oil and water cut measurements were eliminated.

SUMMARY OF THE INVENTION

Briefly, the present invention relates to a new and improved method and apparatus for determining the presence of chlorine in a fluid containing free gas in a petroleum conduit or the like.

The fluid is bombarded with fast neutrons from a neutron source which are slowed down and thereafter engage in thermal neutron capture reactions with materials in the fluid, giving rise to thermal neutron capture gamma rays. The energy spectra of the thermal neutron capture gamma rays for the elements hydrogen and chlorine are obtained, from which a measure of the relative concentration of hydrogen and chlorine in the fluid may be ascertained. From the counting rate for the thermal neutron gamma ray spectra for the element hydrogen, a measure of the hydrogen index (HI) of the fluid is obtained. The hydrogen index of the fluid and the ratio of the relative concentration of chlorine to hydrogen are used to obtain a measure of the presence of chlorine or salt water in the fluid.

In further aspects of the present invention, the concentration of sulfur may also be determined simultaneously with the concentrations of hydrogen and chlorine. Also, since the line temperature, line pressure, hydrogen index of the liquid phase and hydrogen index of the gas phase are usually available or can be monitored, the gas/liquid ratio of the fluid can be computed.

DESCRIPTION OF THE PREFERRED EMBODIMENT

Figure 1:
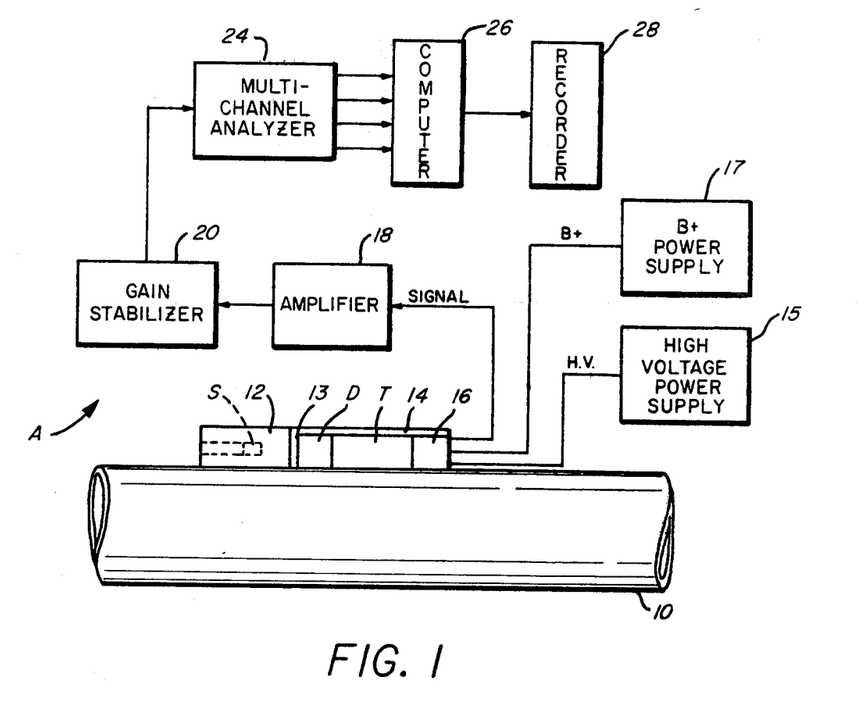
FIGS. 1 and 1A are schematic block diagrams of apparatus according to the present invention.
Figure 1A:
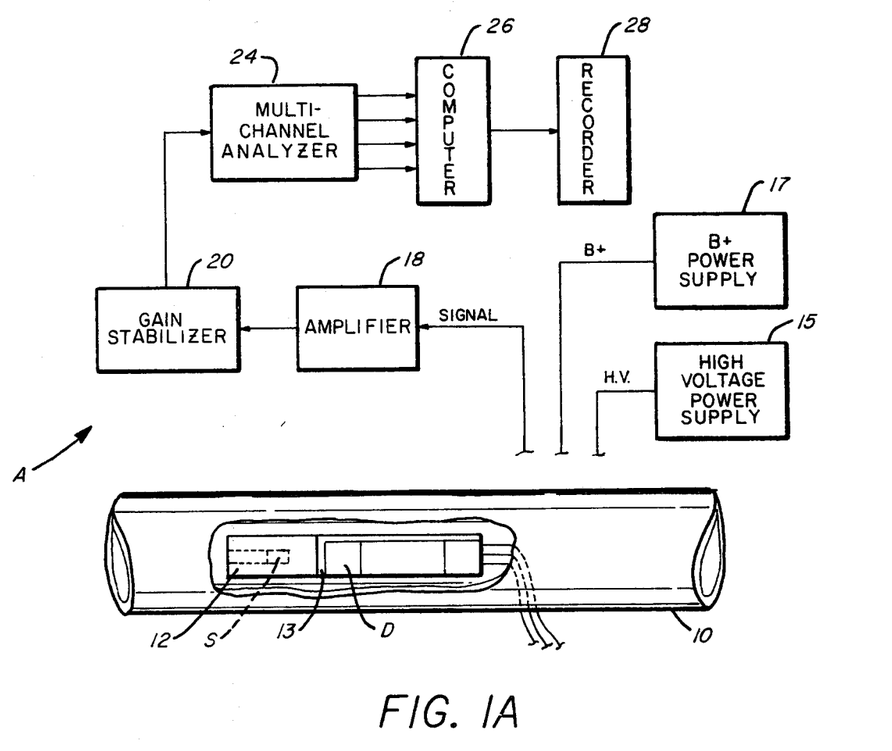

FIG. 1 shows an apparatus A according to the present invention with a neutron source S and a detector D mounted along a common axis mounted adjacent each other on an outer surface of a crude oil flow line 10. The source S and detector D may also, if desired, be mounted within the line 10 along a common axis (FIG. 1A). The source S shown is a Am-B neutron source emitting $1.33 \times 10^7$ neutrons per second, although it should be understood that a different source material such as actinium-beryllium, californium$^{252}$ or americium-beryllium could be used, if desired. The source S is preferably surrounded by a suitable shielding material 12, such as graphite, which thermalizes but does not capture neutrons in order to increase the thermal neutron flux for capture within the fluid of interest. The intervening space 13 between the source S and detector D is also filled with such a material. The detector D is preferably a $2'' \times 4''$ NaI(Tl) cylindrical crystal coupled to a photomultiplier tube T.

It is preferable to enclose the detector D within a sleeve of durable material 14 coated with a coating material of high thermal neutron capture cross-section, such as boron. This is especially true if iron cannot be eliminated in the fabrication in the section of the pipe 10 with which the apparatus A is mounted. When the line 10 is made from steel, it is lined internally with boron or other suitable material in the vicinity of the source S and detector D. This boron coating material reduces the possibility of additional "background" radiation. Boron (boron carbide mixed with epoxy resin) is especially suited for this application since it has a large thermal neutron capture cross section ($\sigma = 775$ barns) and a capture reaction which produces no radiation above 0.5 MeV to interfere with the chlorine measurement to be set forth.

The detector D produces scintillations or discrete flashes of light whenever gamma rays pass therethrough, while the photomultiplier tube T generates in response to each such scintillation a voltage pulse proportional to the intensity of the scintillation. A high voltage power supply 15 is provided for the photomultiplier tube T. A conventional preamplifier circuit 16 receives operating power from a B+ power supply 17 and amplifies the pulses from the photomultiplier tube T and furnishes the amplifier pulses to a further amplifier stage 18.

Figure 2A:
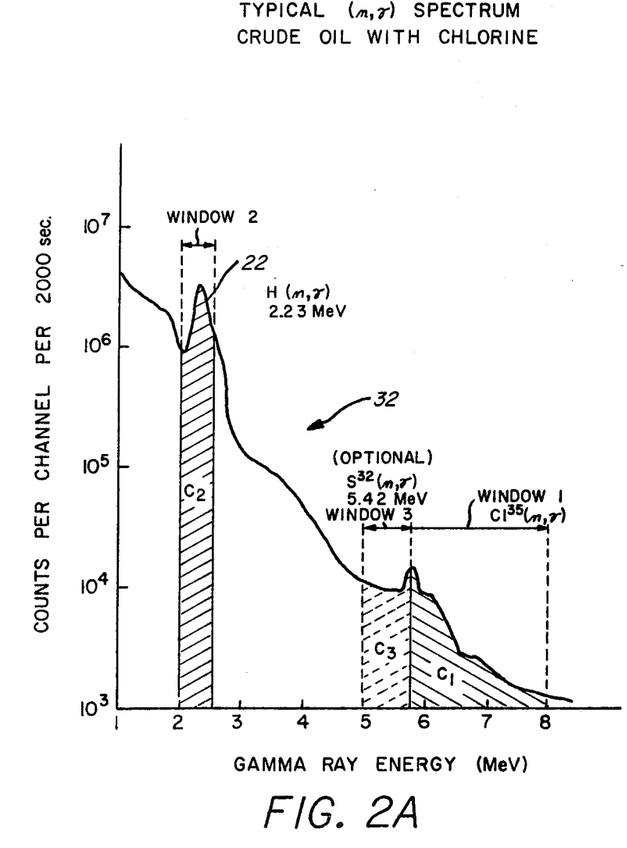
FIGS. 2A and 2B are graphical illustrations of typical thermal neutron capture gamma ray spectra for crude oil.
Figure 2B:
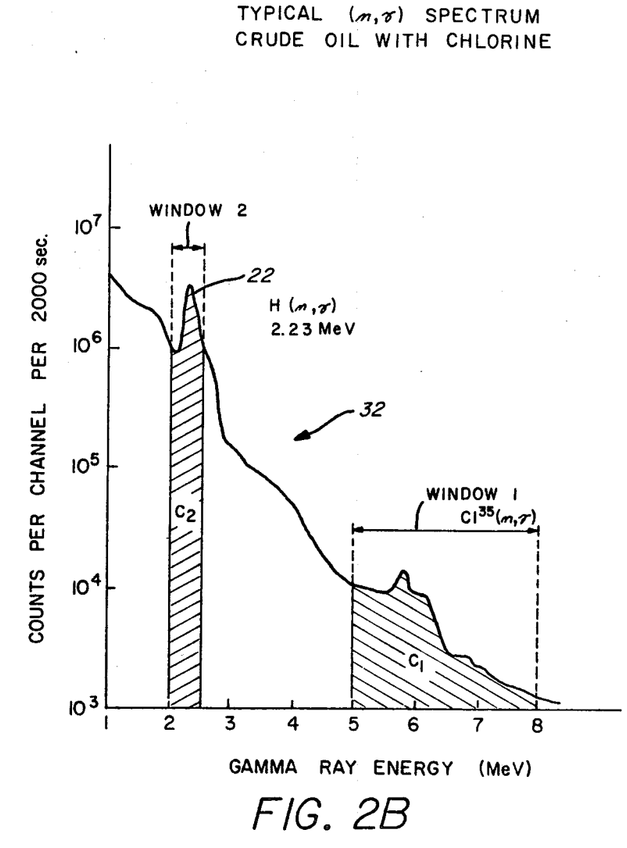

The output pulses from the amplifier 18 are furnished to a gain stabilizer circuit 20 which is calibrated to respond to the energy level of a selected reference peak in the gamma ray energy spectrum, such as the pronounced 2.23 MeV energy peak 22 of hydrogen (FIGS. 2A and 2B). It should be understood, however, that other gamma ray energy peaks, a peak generated from the output of a light emitting diode positioned within the detector crystal D, or a mercury pulser may be used for gain stabilization, if desired. The gain stabilizer circuit 20 is an automatic gain control circuit which responds to energy level of pulses at the calibrated peak level and adjusts the gain of all energy level pulses to compensate for gain shift or variations in tube T and other circuitry of the apparatus of the present invention due to power supply voltage fluctuations and/or temperature effects.

The output pulses from gain stabilizer circuit 20 are supplied to a pulse height or multi-channel analyzer 24. The pulse height analyzer 24 may be of conventional design as known in the art and having, for example, two or more channels or energy divisions corresponding to quantizations or energy ranges of the pulse heights of the input pulses, if desired. The pulse height analyzer 24 functions to sort and accumulate a running total of the incoming pulses into a plurality of storage locations or channels based on the height of the incoming pulses which, it will be recalled, is directly related to the energy of the gamma rays causing the pulse. The output of the pulse height analyzer 24 in the case of the present invention consists of count pulses occurring in each of two energy ranges or windows (or more as depicted in FIG. 2B) or, alternatively three energy ranges or windows (as depicted in FIG. 2A). It should also be understood that two appropriately biased single channel analyzers may be used in place of the multi-channel analyzer 24, if desired.

The output from the pulse height analyzer 24 may be stored on a suitable memory device for subsequent processing, or alternatively, is supplied directly over an appropriate number of lines to a computer 26, which obtains from the number of chlorine counts, the number of hydrogen counts and the length of time for such counts, the water cut of the fluid in the line 10, in a manner to be set forth. Further, the computer 24 may also determine from the output of analyzer 26 other measurements regarding the fluid in line 14, as will be set forth. The results of such computations may be stored or displayed, as desired, with a recorder 28 or other suitable display device.

FIG. 2A shows a typical capture gamma ray spectrum 32 recorded using the equipment of FIG. 1 for a stream of crude oil containing free gas as well as small amounts of chlorine. The intense peak of 2.23 MeV of hydrogen indicated by reference numeral 22 results from the capture of thermal neutrons by hydrogen in the crude oil and may be used, as set forth above, as an energy reference peak by the gain stabilizer circuit of FIG. 1. FIG. 2B also shows energy settings of the multi-channel analyzer 24. The first setting, identified as "Window 1", extends from 5.00 to 8.0 MeV and includes photoelectric and escape peaks from the 7.79, 7.42, 6.64 and 6.11 MeV radiation from the $Cl^{35}$ (n,$\gamma$) $Cl^{36}$ reaction as well as 5.42 MeV sulfur capture peak and the less intense 7.78, 7.42, 7.19, 6.64 and 5.97 MeV peaks from sulfur. The second setting, identified as "Window 2", extends from 2.05 to 2.50 MeV and includes the 2.23 MeV hydrogen capture peak identified by reference numeral 22.

Relatively small concentrations of salt water in crude oil can often cause major problems in the crude oil refining process. The present invention relates to the detection in a flowing multiphase fluid crude oil stream, or other petroleum conduit, of the amount of salt in the fluid while eliminating the effects of gas, such as free gas, in the fluid on the measurements.

In the prior U.S. patents referenced above, the space between the neutron source and the gamma ray detector was filled with the fluid of interest. Such a source-detector geometry produced the maximum salt detection sensitivity and introduced no problems in the accuracy of the measurement so long as the fluid contained no free gas. In addition, the fluid served as a constant density shield between the detector and the direct neutron flux from the source. Although the fluid did not completely shield the detector, the source-induced background remained constant.

If, however, free gas is present in the fluid in pipe 10 the shielding properties of the fluid are decreased depending upon the fraction and homogeneity of the free gas-liquid mixture. This varies the source-induced background level which, in turn, significantly degrades the accuracy of the liquid phase salt content measurement.

According to the present invention, the adverse effects of the variable neutron-induced background can be minimized, though, by filling the space between source S and detector D with fixed graphite shielding material rather than the fluid of interest. Some precision may be lost with this source-detector geometry; however, in the presence of free gas, the accuracy of the salt content measurement is superior to that obtained with the source and detector on opposite sides of the flow pipe 10.

In a test of the present invention, a section of fiberglas pipe 10 was filled with 45,850 cm³ of tap water which contained approximately 25 pounds per thousand barrels (PTB) of NaCl. A series of gamma ray spectra were recorded so that the observed as well as statistical standard deviation could be computed. $R_{Cl}$, the ratio of count rate $C_{Cl}$ recorded in the energy region 5.75 to 8.0 MeV (chlorine window) (FIG. 2A) to the count rate $C_H$ recorded in the energy region 2.05 to 2.50 MeV (hydrogen window), was computed for each spectrum. Known amounts of chlorine, $M_{Cl}$, in the form of NaCl were added to the water in increments. Following each addition, the above counting sequence was repeated.

Void spaces representing free gas were introduced within the pipe 10, having 10⅝ inch diameter, by displacing a portion of the liquid with thin walled, air filled acrylic resin tubes mounted at selected locations within the cross-sectional area of the pipe 10 and extending from the source S to the detector D. Acrylic resin tubes were used because the neutron properties of some acrylic resin, such as that sold under the Du Pont trademark Lucite, are almost identical to those of fresh water. Groups of 21, 40, and 49 tubes were arranged in regular arrays to simulate homogeneous fluids with hydrogen indices, HI=0.83, 0.68, and 0.61, respectively. The gamma ray counting sequence was repeated at each hydrogen index using water with various salinities.

Hydrogen index, HI, is proportional to the quantity of hydrogen per unit volume of fluid with the hydrogen index of fresh water taken as unity. HI is related to the gas phase fraction $V_g$ by the relation:

$$V_g = \frac{(HI)_L - HI}{(HI)_L - (HI)_g} \quad (1)$$

where $(HI)_L$ and $(HI)_g$ are the hydrogen indicies of the liquid and gas phases, respectively.

Fluids with HI=0.47, 0.39, 0.20, and 0.11 were simulated by arranging water filled tubes in regular arrays of 49, 40, 21, and 12, respectively, with the pipe 10 empty. Again, the counting sequence was repeated for each array using water with various salinities.

Figure 3:
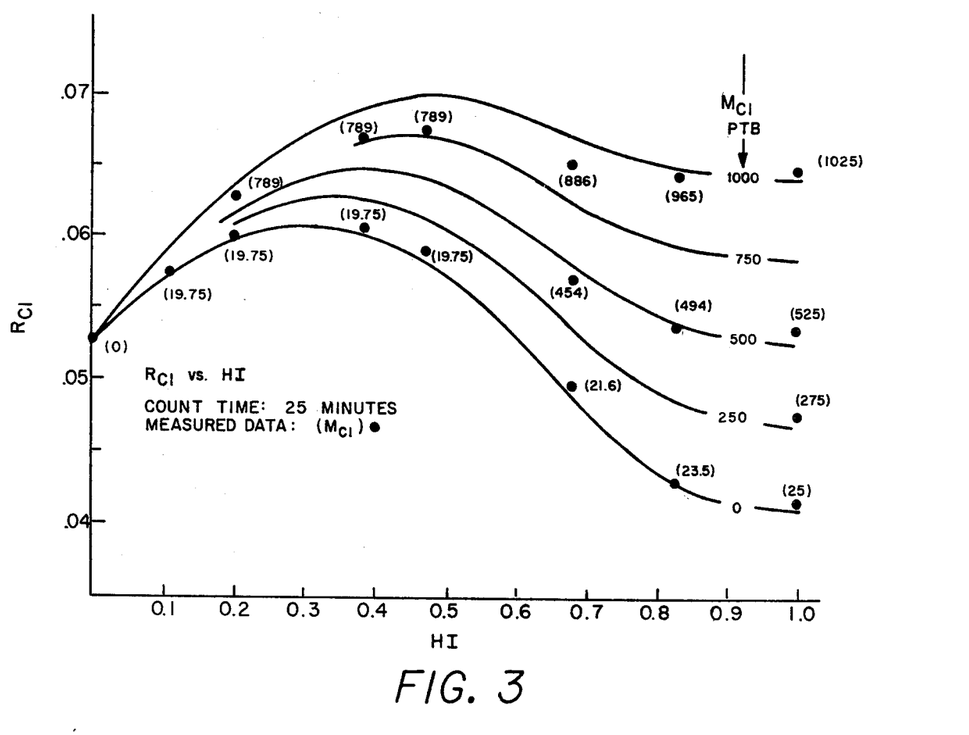
FIG. 3 is a graphical illustration showing the count rate ratio in chlorine detection energy windows to that of hydrogen energy windows as a functions of hydrogen index.

FIG. 3 shows a plot of the measured quantity $R_{Cl}$, as a function of HI for measures of the relative presence of chlorine, $M_{Cl}$, expressed in PTB. Each data point represents a total count time of 25 minutes with the number in parenthesis indicating $M_{Cl}$, the salinity of the liquid phase in PTB. The constant salinity curves were obtained by least-squares fitting all available data. It can be seen from the spread of these curves that the precision to which $M_{Cl}$ can be measured increases as the HI of the fluid increases.

Figure 4:
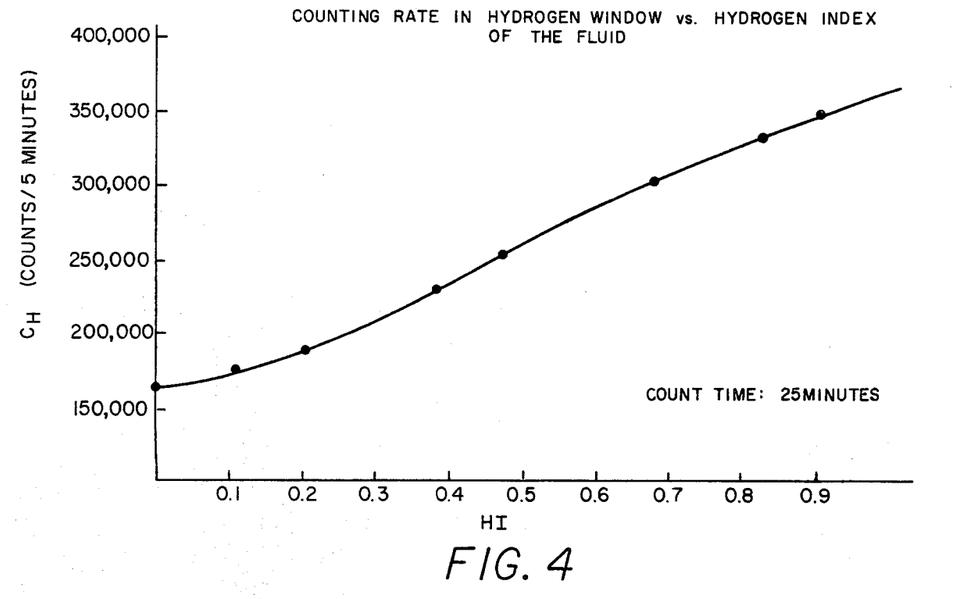
FIG. 4 is a graphical illustration of counting rate in hydrogen energy windows as a function of hydrogen index.

FIG. 4 shows a plot of observed hydrogen window count rate $C_H$ as a function of HI. Based on a measured $C_H$ in window 2 (FIG. 2A) the hydrogen index HI for the multiphase fluid under test may be readily determined. It is to be noted that the relationship between hydrogen count $C_H$ and hydrogen index HI is nearly linear as can be theoretically predicted.

Figure 5:
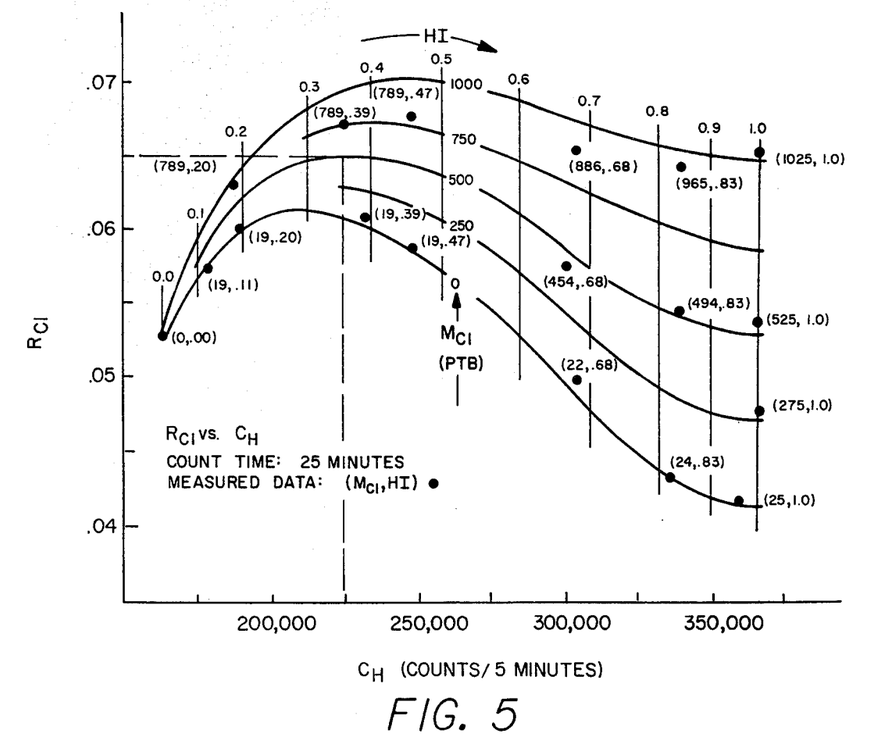
FIG. 5 is a graphical illustration showing hydrogen index and relative presence of chlorine as functions of the count rate ratio in chlorine detection energy windows to that of hydrogen energy windows and of the hydrogen count rate.

FIG. 5 shows a plot of $R_{Cl}$ as a function of $C_H$ and is a compilation of information presented in FIGS. 3 and 4. The numbers in parenthesis indicate the values of $M_{Cl}$ and HI, respectively, which correspond to each data point. It should be noted that both $R_{Cl}$ and $C_H$ are measured quantities in the apparatus A. These quantities, along with a chart of the form of FIG. 5, can be used to determine $M_{Cl}$ (and HI) for any unknown fluid. As an example, recorded values of $C_H$=225,000 counts/5 minutes and $R_{Cl}$=0.065 indicate a fluid with a liquid phase salinity $M_{Cl}$=500 PTB and a hydrogen index HI=0.36.

Figure 6:
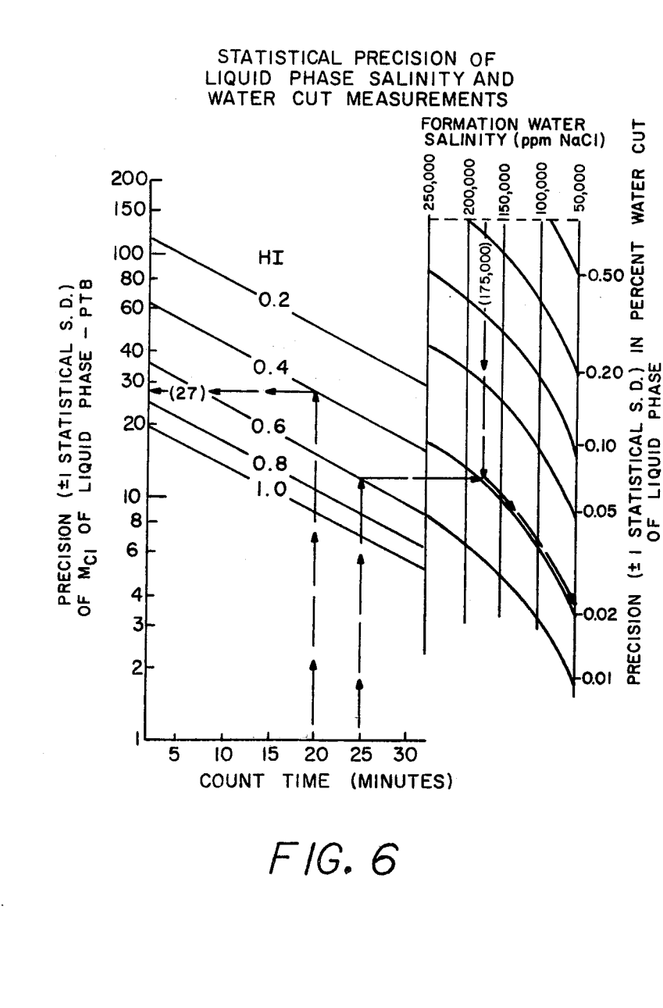
FIG. 6 is a graphical illustration of percent standard deviation of results of the present invention.

FIG. 6 can be used to estimate the statistical precision to which $M_{Cl}$ can be measured using the apparatus shown in FIG. 1. As an example, for a fluid with HI=0.4 and a count time of 20 minutes, the statistical standard deviation of the $M_{Cl}$ measurement is ±27 PTB. Precision in terms of percent water cut in an oil-water liquid phase can be estimated using the right hand side of FIG. 6. As an example, for a fluid with HI=0.6, a salt water phase salinity of 175,000 ppm NaCl, and a count time of 25 minutes, the percent water cut of the liquid phase can be measured to ±0.02%.

It should be noted that the chart in FIG. 6 represents maximum precisions that can be expected. Actual precision in a homogenous fluid would be degraded 10 to 20% by systematic errors in the gamma ray detection equipment. In addition, the precision would be degraded if the measurements were made through steel rather than Fiberglas pipe.

To determine the test on non-homogeneous gas mixing further tests were performed in the fluid with the acrylic resin tubes geometrically grouped adjacent, diametrically opposite and at a 90° angle (quadrature) within the pipe 10 with respect to the apparatus A on the periphery on the pipe 10. The geometry, hydrogen index (HI) of the fluid, salinity of the liquid phase, and corresponding symbols are tabulated in the chart below.

CHART I

| SYMBOL | GEOMETRY | HI | $M_{Cl}$(PTB) | TUBE FLUID |
|---|---|---|---|---|
| 1a | ADJACENT | 0.92 | 24 | AIR |
| 2a | QUADRATURE | 0.92 | 24 | AIR |
| 3a | OPPOSITE | 0.92 | 24 | AIR |
| 1b | ADJACENT | 0.82 | 23 | AIR |
| 2b | QUADRATURE | 0.82 | 23 | AIR |
| 3b | OPPOSITE | 0.82 | 23 | AIR |
| 1c | ADJACENT | 0.71 | 22 | AIR |
| 2c | QUADRATURE | 0.71 | 22 | AIR |
| 3c | OPPOSITE | 0.71 | 22 | AIR |
| 1d | ADJACENT | 0.35 | 19 | WATER |
| 2d | QUADRATURE | 0.35 | 19 | WATER |
| 3d | OPPOSITE | 0.35 | 19 | WATER |
| 1e | ADJACENT | 0.22 | 19 | WATER |
| 2e | QUADRATURE | 0.22 | 19 | WATER |
| 3e | OPPOSITE | 0.22 | 19 | WATER |
| 1f | ADJACENT | 0.82 | 945 | AIR |
| 2f | QUADRATURE | 0.82 | 945 | AIR |
| 3f | OPPOSITE | 0.82 | 945 | AIR |

Figure 9:
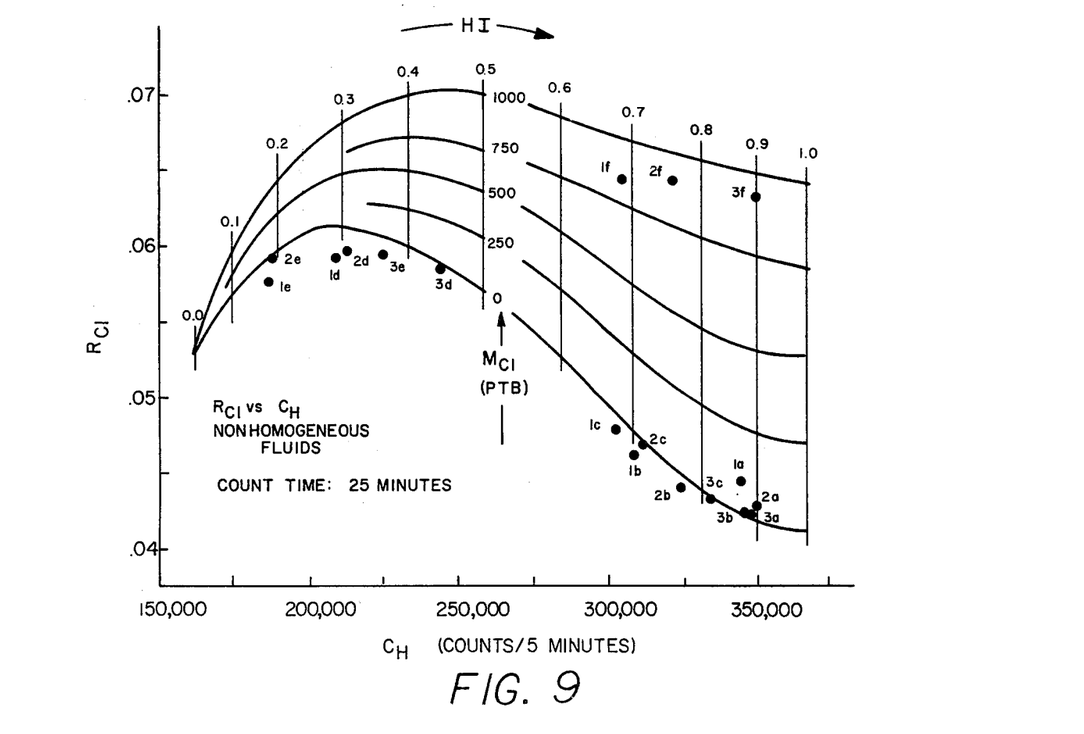
FIG. 9 is a graphical illustration showing hydrogen index and relative presence of sulfur as functions of the count rate ratio in chlorine detection energy windows to that of hydrogen energy windows and of the hydrogen count rate for various non-homogenous fluids.

The values of $R_{Cl}$ are plotted as a function of $C_H$ in FIG. 9 for each nonhomogeneous fluid. The solid curves in FIG. 9 are constant salininty curves, $M_{Cl}$, and constant hydrogen index curves, HI, obtained from least-squares fitting data in the homogeneous fluids of FIG. 3. It can be seen from FIG. 9 that, within the limits of experimental error, the data points fall along the proper $M_{Cl}$ curves. This indicates that, even though the mixture is nonhomogeneous, an accurate salinity measurement can be made with the present invention.

The fluid hydrogen index HI read from FIG. 9 is a function of the position of the source-detector assembly relative to the location of the fluid inhomogeneity. If we define $HI_j$ as the hydrogen index measured with the source-detector assembly at position j=1 (for Adjacent), 2 (for Quadrature) or 3 (for Opposite), if can be determined that $$(HI_1 + 2HI_2 + HI_3)/4 \quad (2)$$

closely represents the true hydrogen index of the non-homogeneous fluid. This indicates that if the gas and liquid phases of nonhomogeneous fluids "wander" randomly within the flow line with a frequency much shorter than the counter time, then the "average" measured hydrogen index would closely represent the true hydrogen index of the fluid. This criterion can be met in many oil field situations by choosing an advantageous location (such as a riser) on which to install the apparatus A.

Additional chlorine capture gamma radiation occurs within the energy region 5.00 to 5.75 MeV. The statistical precision of the $M_{Cl}$ measurement can, therefore be improved by reducing the low bias of the chlorine window from 5.75 MeV to 5.00 MeV (FIG. 2B). As discussed in U.S. Pat. No. 4,200,789, sulfur produces interfering radiation at 5.41 MeV which would, however, be included in such an enlarged chlorine window. For a chlorine window of 5.00 to 8.00 MeV, a 1% variation in sulfur content of the liquid phase appears as a 37 PTB variation in the $M_{Cl}$ measurement. If, however, the sulfur content of the crude is known and remains relatively constant, the apparatus A can be calibrated for a specific sulfur concentration.

Figure 7:
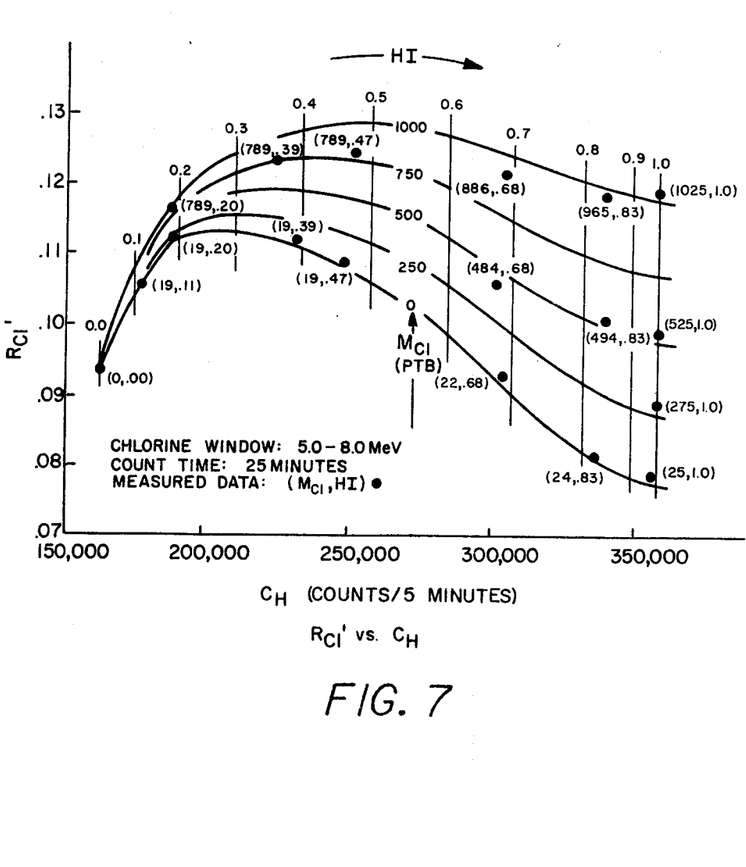
FIG. 7 is a graphical illustration showing the count rate ratio in chlorine detection energy windows to that of hydrogen energy windows as a function of hydrogen count rate for an enlarged hydrogen energy window of FIG. 2B.

FIG. 7 shows a plot of $R_{Cl}'$ as a function of $C_H$ where $R_{Cl}'$ is defined as the ratio of count rate recorded in energy region 5.00 to 8.00 MeV to the hydrogen count rate $C_H$. Each data point represents a total count time of 25 minutes with the numbers in brackets again indicating $M_{Cl}$ and HI, respectively. Error propagation calculations show that the statistical precision read from FIG. 6 are improved an additional 21% using the larger chlorine window of FIG. 2B.

It should be noted that, in obtaining the salt content of the liquid phase of the fluid, the hydrogen index, HI, of the fluid is also obtained. If the gas and liquid phases of the fluid are moving past the apparatus A at the same velocity and if the following additional information is available or is monitored:
(1) line temperature
(2) line pressure
(3) hydrogen index of the liquid phase
(4) hydrogen index of the gas phase
the gas/liquid ratio can be computed.

It should also be noted that the sulfur content of the liquid phase, $M_S$, can be determined simultaneously with the salt content $M_{Cl}$ and HI by determining, in accordance with U.S. Pat. No. 4,209,695 an additional ratio $$R_S = \frac{\text{COUNT RATE RECORDED IN ENERGY WINDOW 3 (FIG. 2A)}}{\text{COUNT RATE RECORDED IN ENERGY WINDOW 2 (FIG. 2A)}}$$

where window 2 extends from 5.75 to 8.00 MeV and window 3 extends from 5.00 to 5.75 MeV.

Figure 8:
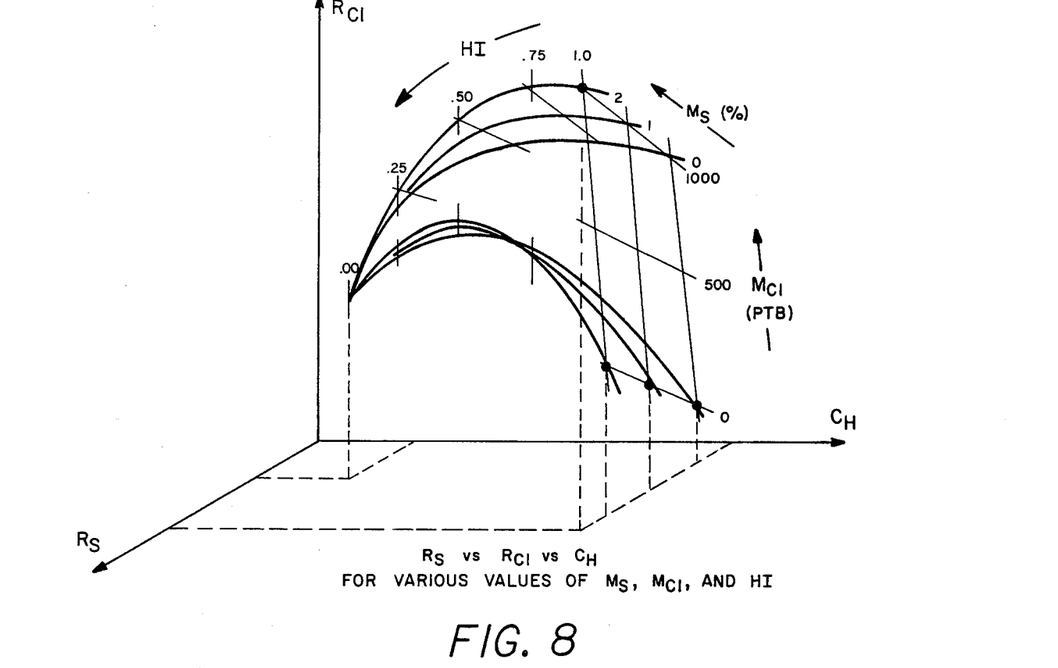
FIG. 8 is a graphical illustration showing hydrogen index and relative presence of sulfur as functions of the count rate ratios of sulfur and chlorine energy windows to that of the hydrogen energy windows and of the hydrogen count rate.

This ratio, $R_s$, along with $R_{Cl}$ and $C_H$ are entered into a plot shown in FIG. 8 to determine $M_{Cl}$, $M_S$, and HI.

The foregoing disclosure and description of the invention are illustrative and explanatory thereof, and various changes in the size, shape and materials, as well as in the details of the illustrated construction may be made without departing from the spirit of the invention.

We claim:

1. A method for analysis of a multiphase fluid, containing liquid and free gas, flowing in a conduit to determine the salt content of the fluid, comprising the steps of:
   (a) bombarding the fluid with fast neutrons which are slowed down and thereafter engage in thermal neutron capture reactions with materials in the fluid;
   (b) obtaining gamma ray energy spectra of the materials in response to the capture of thermal neutrons by the materials in the fluid;
   (c) obtaining a measure of the concentration of hydrogen in the fluid from the gamma ray energy spectra;
   (d) obtaining from the measure of hydrogen concentration the hydrogen index of the fluid;
   (e) obtaining a measure of the concentration of chlorine in the fluid from the gamma ray energy spectra;
   (f) obtaining a ratio of the concentration of chlorine to the concentration of hydrogen; and
   (g) obtaining from the concentration ratio of chlorine to hydrogen and the hydrogen index of the fluid a measure of the salt content of the fluid.

2. The method of claim 1, wherein said step of obtaining gamma ray energy spectra includes:
   obtaining gamma rays from hydrogen in the range of from 2.05 MeV to 2.50 MeV.

3. The method of claim 1, wherein said step of obtaining gamma ray energy spectra includes:
   obtaining gamma rays from chlorine in the range of from 5.75 MeV to 8.0 MeV.

4. The method of claim 1, wherein said step of obtaining gamma ray energy spectra includes:
   obtaining gamma rays from chlorine in the range of from 5.00 MeV to 8.0 MeV.

5. The method of claim 1, further including the step of:
   obtaining a measure of the concentration of sulfur in the fluid from the gamma ray spectra.

6. The method of claim 5, wherein said step of obtaining gamma ray spectra includes:
   obtaining gamma rays from sulfur in the range of from 5.00 MeV to 5.75 MeV.

7. An apparatus for analyzing a multiphase fluid, containing liquid and free gas, flowing in a conduit to determine the salt content of the fluid, comprising:
   (a) means for bombarding the fluid with fast neutrons which are slowed down and thereafter engage in thermal neutron capture reactions with materials in the fluid;
   (b) means for obtaining gamma ray energy spectra of the materials in response to the capture of thermal neutrons by the materials in the fluid;
   (c) means for obtaining a measure of the concentration of hydrogen in the fluid from the gamma ray energy spectra;
   (d) means for obtaining from the measure of hydrogen concentration the hydrogen index of the fluid;
   (e) means for obtaining a measure of the concentration of chlorine in the fluid from the gamma ray energy spectra;
   (f) means for obtaining a ratio of the concentration of chlorine to the concentration of hydrogen; and
   (g) means for obtaining from the concentration ratio of chlorine to hydrogen and the hydrogen index of the fluid a measure of the salt content of the fluid.

8. The apparatus of claim 7, wherein said means for obtaining gamma ray energy spectra includes:
   means for obtaining gamma rays from hydrogen in the range of from 2.05 MeV to 2.50 MeV.

9. The apparatus of claim 7, wherein said means for obtaining gamma ray energy spectra includes:
   means for obtaining gamma rays from chlorine in the range of from 5.75 MeV to 8.0 MeV.

10. The apparatus of claim 7, wherein said means for obtaining gamma ray energy spectra includes:
    means for obtaining gamma rays from chlorine in the range of from 5.00 MeV to 8.0 MeV.

11. The apparatus of claim 7, further including:

means for obtaining a measure of the concentration of sulfur in the fluid from the gamma ray spectra.

12. The apparatus of claim 11, wherein said means for obtaining gamma ray spectra includes:
means for obtaining gamma rays from sulfur in the range of from 5.00 MeV to 5.75 MeV.

13. An apparatus for analyzing a multiphase fluid, containing liquid and free gas, flowing in a conduit to determine the salt content of the fluid, comprising:
(a) a neutron source for bombarding the fluid with fast neutrons which are slowed down and thereafter engage in thermal neutron capture reactions with materials in the fluid;
(b) a gamma ray detector mounted along a common axis adjacent said neutron source on an outer surface of the conduit for obtaining gamma ray energy spectra of the materials in response to the capture of thermal neutrons by the materials in the fluid.

14. The apparatus of claim 13, wherein said neutron source is surrounded by a graphite shielding material.

15. The apparatus of claim 13, wherein said neutron source is an americium-boron neutron source.

16. The apparatus of claim 13, wherein said gamma ray detector is enclosed within a sleeve material having a high thermal neutron capture cross section.

17. The apparatus of claim 16, wherein said sleeve material is boron carbide mixed with epoxy resin.

18. The apparatus of claim 13, wherein said source and said detector are separated by a space from each other and wherein said space is filled by a graphite shielding material.

* * * * *